(12) United States Patent
Shito

(10) Patent No.: US 10,596,543 B2
(45) Date of Patent: Mar. 24, 2020

(54) LIGHT ILLUMINATING APPARATUS

(71) Applicant: HOYA CANDEO OPTRONICS CORPORATION, Toda-shi, Saitama (JP)

(72) Inventor: Kazutaka Shito, Toda (JP)

(73) Assignee: HOYA CANDEO OPTRONICS CORPORATION, Toda-Shi, Saitama (JP)

( * ) Notice: Subject to any disclaimer, the term of this patent is extended or adjusted under 35 U.S.C. 154(b) by 229 days.

(21) Appl. No.: 15/884,312

(22) Filed: Jan. 30, 2018

(65) Prior Publication Data

US 2018/0214843 A1 Aug. 2, 2018

(30) Foreign Application Priority Data

Jan. 31, 2017 (JP) .................................. 2017-016371

(51) Int. Cl.
*B01J 19/12* (2006.01)
*A61L 2/26* (2006.01)
(Continued)

(52) U.S. Cl.
CPC .............. *B01J 19/123* (2013.01); *A61L 2/26* (2013.01); *C03C 25/12* (2013.01); *C03C 25/24* (2013.01); *C03C 25/6226* (2013.01); *G02B 6/02395* (2013.01); *G02B 19/0028* (2013.01); *G02B 19/0095* (2013.01); *A61L 2/10* (2013.01);
(Continued)

(58) Field of Classification Search
CPC .............. B01J 19/123; B01J 2219/0869; B01J 2219/0871; B01J 2219/0879; B01J 2219/1203; A61L 2/26; A61L 2/10; A61L 2202/11; C03C 25/12; C03C 25/24; C03C 25/6226; C03C 25/104; C03C 2218/32;
(Continued)

(56) References Cited

U.S. PATENT DOCUMENTS

2011/0147356 A1 6/2011 Leonhardt et al.
2014/0029300 A1* 1/2014 Yuki ...................... G02B 6/002
362/611
(Continued)

FOREIGN PATENT DOCUMENTS

EP 3190441 A1 7/2017
JP H07-072358 A 3/1995
(Continued)

*Primary Examiner* — Nicole M Ippolito

(57) ABSTRACT

A light irradiation device includes a light source having a plurality of solid-state elements disposed on a substrate to be defined by a first direction and a second direction in a plurality of rows and irradiate the irradiation target with light from a third direction, an optical element refracting light from the solid-state elements, emitting the light and narrowing a spread angle of light to be emitted from the solid-state elements relative to the third direction, a first reflection portion having at least two first reflection surfaces on a downstream side in the third direction of the irradiation target and reflecting a part of light incident on the first reflection surface to the irradiation target, and a second reflection portion having a pair of second reflection surfaces disposed between the optical element and the first reflection portion and guiding light from the optical element to the first reflection surface.

21 Claims, 10 Drawing Sheets

(51) Int. Cl.
  *A61L 2/10* (2006.01)
  *G02B 6/02* (2006.01)
  *G02B 19/00* (2006.01)
  *B05D 3/06* (2006.01)
  *C03C 25/104* (2018.01)
  *C03C 25/6226* (2018.01)
  *C03C 25/24* (2018.01)
  *C03C 25/12* (2006.01)

(52) U.S. Cl.
  CPC .... *A61L 2202/11* (2013.01); *B01J 2219/0869* (2013.01); *B01J 2219/0871* (2013.01); *B01J 2219/0879* (2013.01); *B01J 2219/1203* (2013.01); *B05D 3/067* (2013.01); *C03C 25/104* (2013.01); *C03C 2218/32* (2013.01)

(58) Field of Classification Search
  CPC ............ G02B 6/02395; G02B 19/0028; G02B 19/0095; B05D 3/067

USPC ................... 250/493.1, 494.1, 504 R, 504 H
See application file for complete search history.

(56) References Cited

U.S. PATENT DOCUMENTS

| | | |
|---|---|---|
| 2015/0028020 A1 | 1/2015 | Childers |
| 2017/0317243 A1* | 11/2017 | Park ..................... H01L 33/486 |
| 2018/0351044 A1* | 12/2018 | Zhu ....................... H01L 33/405 |
| 2018/0364414 A1* | 12/2018 | Saccomanno ........ G02B 6/0095 |

FOREIGN PATENT DOCUMENTS

| | | |
|---|---|---|
| JP | 2004-121577 A | 4/2004 |
| JP | 2013-527554 A | 6/2013 |
| JP | 2014-075323 A | 4/2014 |
| JP | 2016-034746 A | 3/2016 |
| JP | 2016-534967 A | 11/2016 |
| JP | 2017-122906 A | 7/2017 |

* cited by examiner

LIGHT ILLUMINATING APPARATUS

TECHNICAL FIELD

The present invention relates to a light irradiation device which irradiates an irradiation target capable of relatively moving along a predetermined direction with light, for example, a device for curing a coating agent coated on an optical fiber.

BACKGROUND ART

Conventionally, in the process of manufacturing an optical fiber, an ultraviolet-curable coating agent is coated on the surface of the optical fiber in order to protect the surface of the drawn optical fiber and to maintain the strength of the optical fiber. Such a coating agent is coated in an uncured state by a coating device and cured by a light irradiation device from which ultraviolet light radiates (for example, Patent Document 1).

Patent Document 1 describes a device for curing a coating material by allowing a drawn optical fiber coated with the coating material (coating agent) to pass through a curing chamber having an elliptic housing. The interior of the elliptic housing is provided with an elliptical mirror and a quartz halogen lamp extended in parallel to the path of the optical fiber and constituted to respectively dispose the quartz halogen lamp and the optical fiber at the first focal position and the second focal position of the elliptical mirror so that ultraviolet light to radiate from the quartz halogen lamp reliably hits the outer circumference of the optical fiber.

RELATED DOCUMENTS

Patent Documents

Patent Document 1: Japanese Patent Publication No. 1995-72358A

DISCLOSURE

Technical Problem

Summary of the Invention

Problem to be Solved by the Invention

According to the device described in Patent Document 1, ultraviolet light from the quartz halogen lamp and discharge lamp disposed at the first focal position of the elliptical mirror reflects from the elliptical mirror and is reliably guided to the optical fiber disposed at the second focal position of the elliptical mirror.

However, the device described in Patent Document 1 has a problem that the entire device increases in size since it is required to condense the light to radiate from the bright point of the discharge lamp at 360° to the optical fiber and it is thus required to provide an elliptical mirror so as to surround the discharge lamp and the optical fiber and also to provide a predetermined distance between the first focal position and the second focal position of the elliptical mirror. In addition, it is more desirable as the irradiation intensity by ultraviolet light is higher in order to reliably cure the coating agent of the optical fiber, but it is difficult to increase the irradiation intensity by ultraviolet light since the irradiation intensity by ultraviolet light is determined by the performance of the discharge lamp and the design of the elliptical mirror in the configuration of Patent Document 1.

The present invention has been made in view of the above circumstances, and an object thereof is to provide a light irradiation device capable of irradiating the entire outer circumference surface of an irradiation target such as an optical fiber with light providing a high irradiation intensity without using an elliptical mirror while being small in size.

Technical Solution

In order to achieve the above object, the light irradiation device of the present invention is a light irradiation device which irradiates an irradiation target capable of relatively moving along a first direction with light and includes a substrate to be defined by the first direction and a second direction orthogonal to the first direction, a light source having a plurality of solid-state elements which are disposed on the substrate in a plurality of rows along the first direction and irradiate the irradiation target with the light from a third direction orthogonal to the first direction and the second direction, an optical element which is disposed in an optical path of the plurality of solid-state elements and refracts light from each of the solid-state elements at a predetermined angle and emits the light as well as narrows a spread angle of light to be emitted from each of the solid-state elements with respect to the third direction, a first reflection portion which has at least two first reflection surfaces disposed on a downstream side in the third direction of the irradiation target when viewed from the first direction and reflects a part of light incident on the first reflection surface from the optical element to the irradiation target, and a second reflection portion which has a pair of second reflection surfaces disposed between the optical element and the first reflection portion and guides the light from the optical element to the first reflection surface.

According to such configuration, it is possible to reliably irradiate the outer circumference of an irradiation target with light since the side of the irradiation target facing the light source is directly irradiated with the light from the light source and the side of the irradiation target not facing the light source is irradiated with the light reflecting from the first reflection portion. In addition, it is possible to irradiate the entire outer circumference surface of the irradiation target with light providing a high irradiation intensity since the optical element is disposed in the optical path of a plurality of solid-state elements in the configuration. In addition, the entire outer circumference surface of the irradiation target is irradiated with ultraviolet light even if the position of the irradiation target is slightly shifted in the second direction or the third direction since ultraviolet light directed in various directions exists in the space between the light source and the first reflection portion. In addition, an elliptical mirror as in the prior art is not required and the light source and the irradiation target can be disposed so that the space therebetween is narrowed more than in the prior art since a solid-state element which emits light spreading to 180° is applied as a light source, and it is thus possible to miniaturize the light irradiation device. In addition, it is possible to suppress the temperature rise as compared with the configuration using a discharge lamp as in the prior art since a solid-state element which does not include a hot wire can be applied as a light source. In addition, it is possible to miniaturize the fan for cooling the light irradiation device and further the light irradiation device itself since the temperature rise of the light irradiation device itself can also be suppressed.

In addition, it is possible to configure the light irradiation device so that a principal ray of the light to be emitted from the plurality of solid-state elements is incident on the first reflection surface or incident on the irradiation target without being incident on the first reflection surface when viewed from the first direction.

In addition, it is possible to configure the light irradiation device so that a perpendicular line passing through a center of the light source substantially coincides with an optical axis of the optical element when viewed from the first direction. In addition, it is desirable that an interval between the plurality of solid-state elements in the second direction widens as a distance from a center of the light source increases in this case.

In addition, it is desirable that the optical element is a cylindrical lens extending in the first direction.

In addition, the light irradiation device can include a pair of third reflection portions which are disposed between the light source and the optical element so as to sandwich an optical path of the plurality of solid-state elements from the second direction and guide the light from the light source to the optical element. In addition, it is desirable that the pair of third reflection portions are inclined with respect to the third direction when viewed from the first direction and an interval between the pair of third reflection portions narrows as a distance from the light source increases in this case.

In addition, the light irradiation device can include a pair of fourth reflection portions to be disposed between the optical element and the second reflection portion so as to sandwich an optical path of the plurality of solid-state elements from the second direction. In addition, it is desirable that the pair of fourth reflection portions are inclined with respect to the third direction when viewed from the first direction and an interval between the pair of fourth reflection portions widens as a distance from the optical element increases in this case.

In addition, it is desirable that the first reflection surface is disposed line-symmetrically with respect to a perpendicular line passing through a center of the light source when viewed from the first direction. In addition, it is desirable that the first reflection surface is a flat surface and is disposed so that a perpendicular bisector of the first reflection surface intersects a perpendicular line passing through a center of the light source when viewed from the first direction in this case.

In addition, it is desirable that the pair of second reflection surfaces are inclined with respect to the third direction when viewed from the first direction and an interval between the pair of second reflection surfaces narrows as a distance from the light source increases.

In addition, it is desirable that the following Mathematical Formula (1) is satisfied when a maximum intensity of the light on an outer circumference surface of the irradiation target is denoted by MAX and a minimum intensity of the light on the outer circumference surface of the irradiation target is denoted by MIN.

$$\text{MIN/MAX} \geq 50\% \quad (1)$$

In addition, the light irradiation device can include a heat dissipation member which is thermally bonded to the first reflection portion and the second reflection portion and dissipates heat from the first reflection portion and the second reflection portion. In addition, it is desirable that the heat dissipation member has a plate shape and a housing portion for housing the first reflection portion and the second reflection portion is formed on one surface of the heat dissipation member in this case. In addition, it is desirable that the heat dissipation member has a plurality of heat dissipation fins on the other surface opposite to the one surface in this case. In addition, it is desirable that the light irradiation device includes a cooling fan for blowing air to the heat dissipation fins in this case.

In addition, it is desirable that the light irradiation device further includes a translucent pipe which extends in the first direction so as to cover the irradiation target and transmits the light from the light source.

In addition, it is desirable that the light is light in an ultraviolet wavelength region.

In addition, it is desirable that the irradiation target has a linear, spherical, or granular shape and light in the ultraviolet wavelength region cures a coating agent coated on an outer circumference surface of the irradiation target.

In addition, it is desirable that the irradiation target is liquid and light in the ultraviolet wavelength region sterilizes the irradiation target.

Advantageous Effects

As described above, according to the present invention, it is possible to realize a light irradiation device capable of irradiating the entire outer circumference surface of an irradiation target such as an optical fiber with light providing a high irradiation intensity without using an elliptical mirror while being small in size.

BEST MODE

Mode for Carrying Out the Invention

Figure 1:
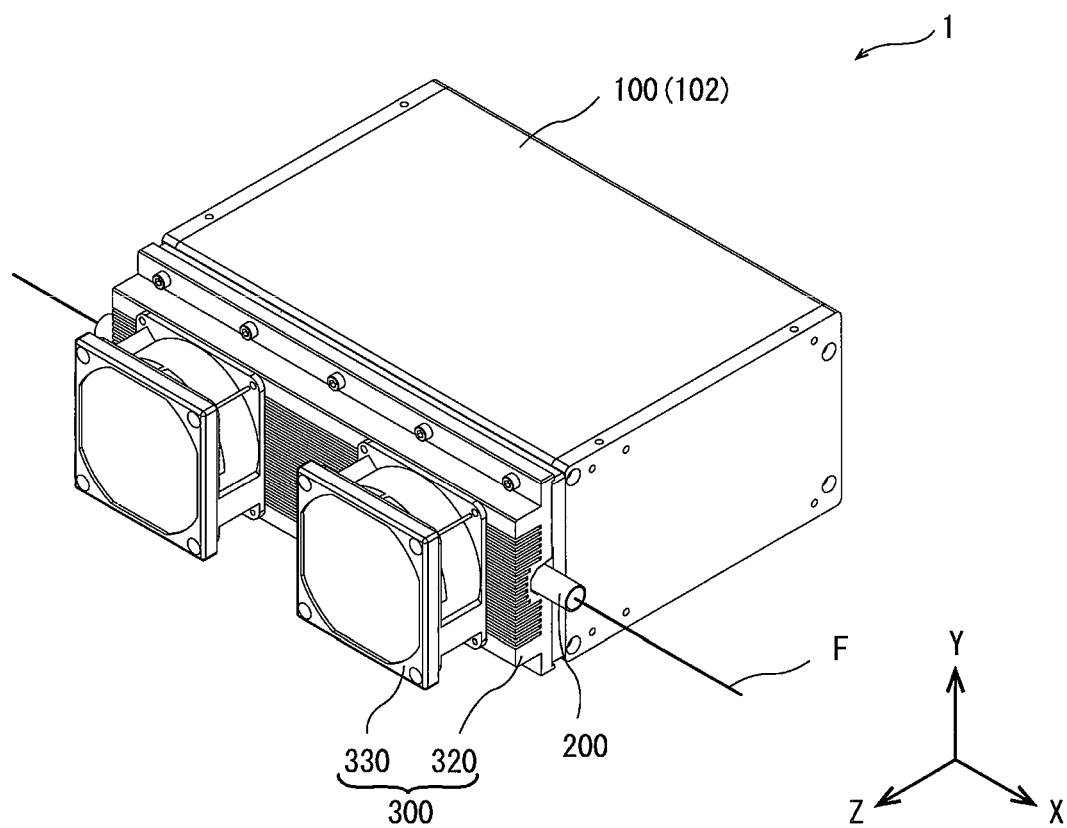
FIG. 1 is an external perspective view illustrating the configuration of a light irradiation device according to a first embodiment of the present invention.

Hereinafter, embodiments of the present invention will be described in detail with reference to the drawings. Incidentally, the same or corresponding parts in the drawings are denoted by the same reference numerals, and the description thereon will not be repeated.

First Embodiment

Figure 2:
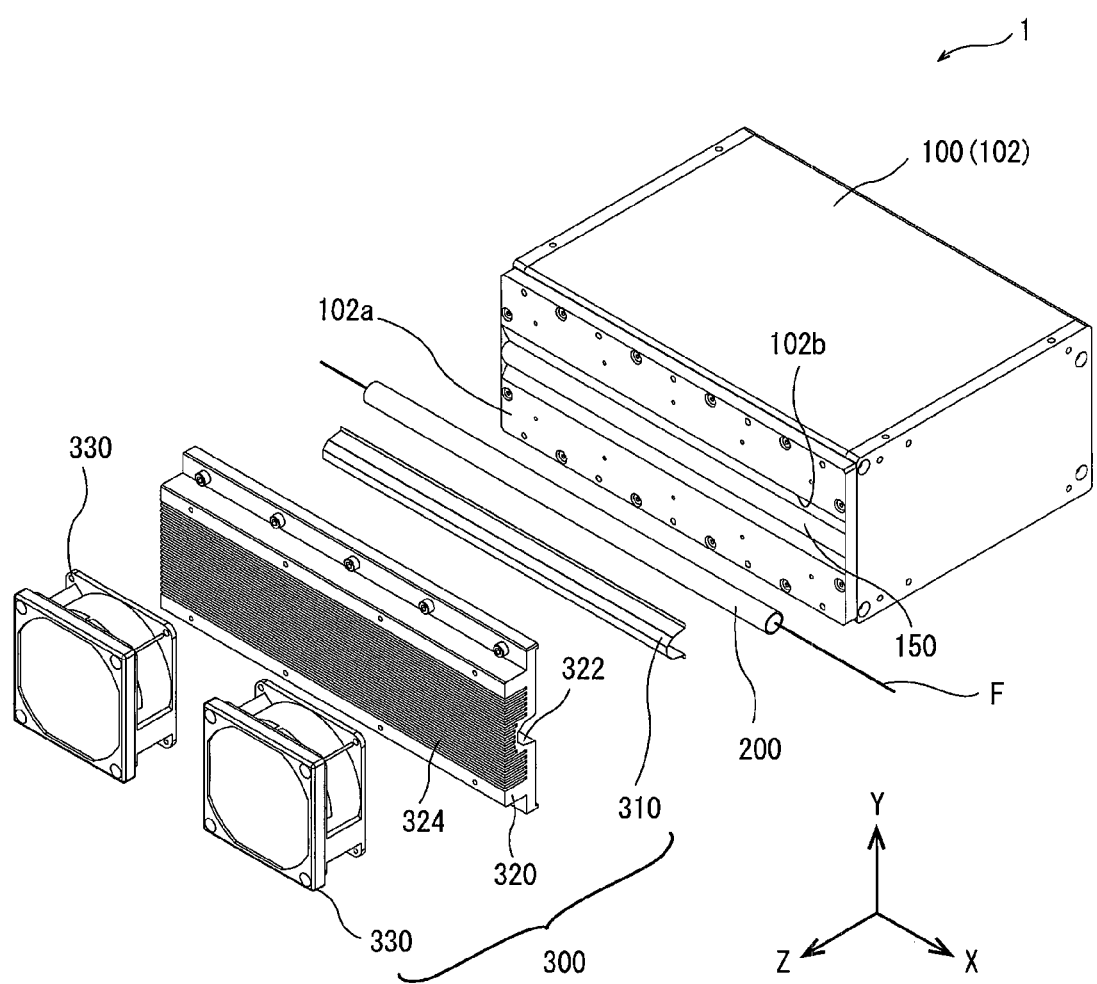
FIG. 2 is an exploded perspective view of the light irradiation device of FIG. 1.

FIG. 1 is an external perspective view illustrating the configuration of a light irradiation device 1 according to a first embodiment of the present invention. In addition, FIG. 2 is an exploded perspective view of the light irradiation device 1. The light irradiation device 1 of the present embodiment is a light source device which cures the coating agent coated on a drawn optical fiber F, and it emits linear ultraviolet light along the optical fiber F moving (running) in one direction. Incidentally, in the present specification, the moving direction of the optical fiber F is defined as the X-axis direction, the direction in which an LED (Light Emitting Diode) element 115 (solid-state element) to be described later emits ultraviolet light is defined as the Z-axis direction, and the direction orthogonal to the X-axis direction and the Z-axis direction is defined as the Y-axis direction as illustrated in the coordinates of FIG. 1 for explanation. In addition, ultraviolet light generally means light having a wavelength of 400 nm or less, but ultraviolet light means light having a wavelength (for example, a wavelength of from 250 to 420 nm) at which a coating agent can be cured in the present specification.

As illustrated in FIG. 1 and FIG. 2, the light irradiation device 1 of the present embodiment is equipped with a light source unit 100, a translucent pipe 200, and a mirror module 300.

Figure 3A:
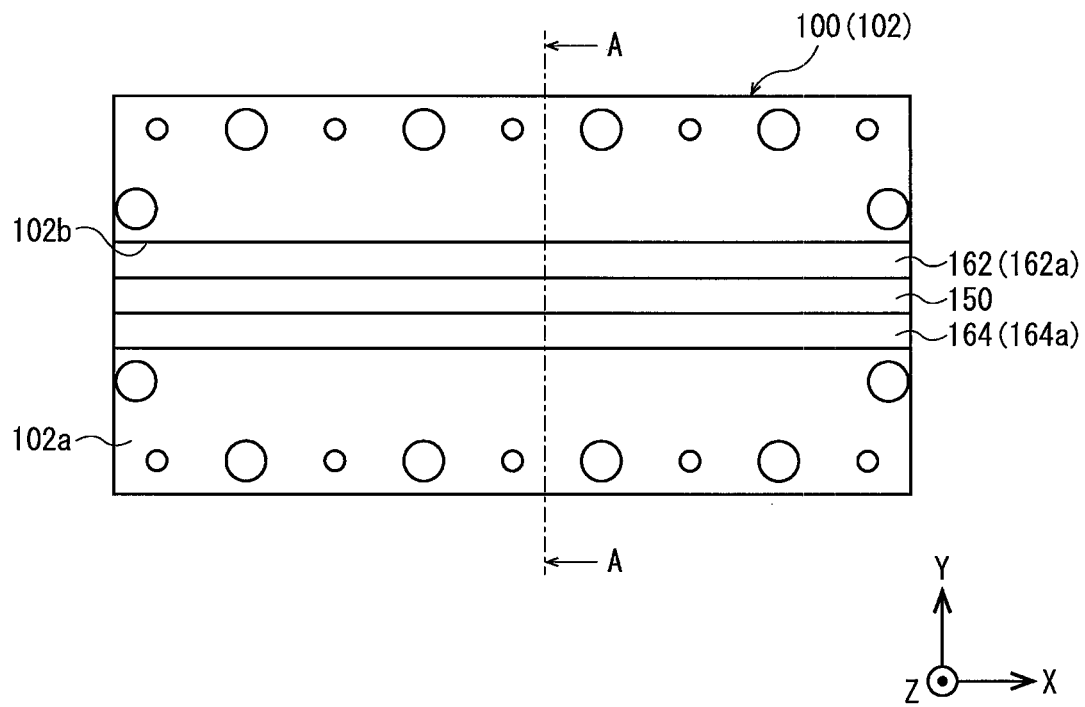
FIGS. 3A and 3B are views illustrating the configuration of a light source unit equipped in a light irradiation device according to a first embodiment of the present invention.
Figure 3B:
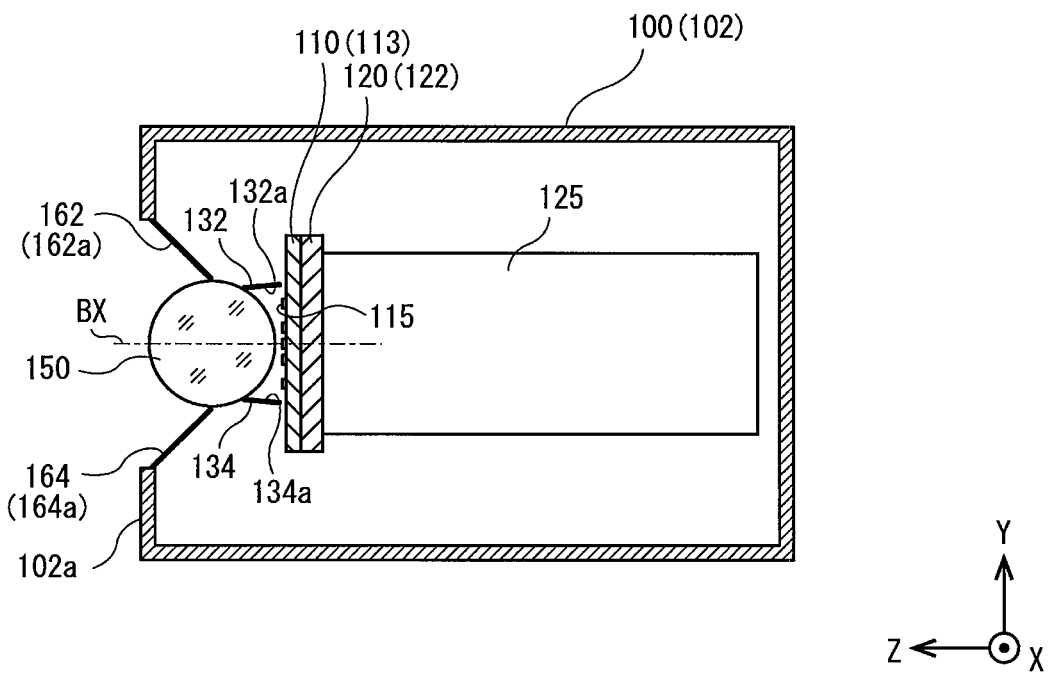
Figure 4A:
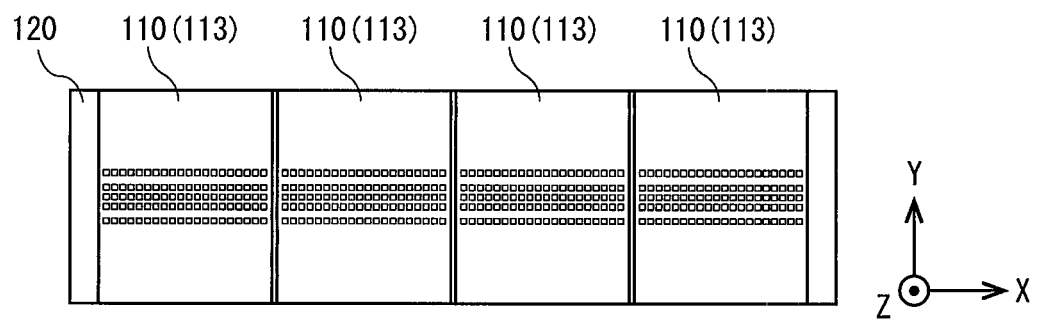
FIGS. 4A and 4B are views illustrating the configuration of an LED module equipped in a light irradiation device according to a first embodiment of the present invention.
Figure 4B:
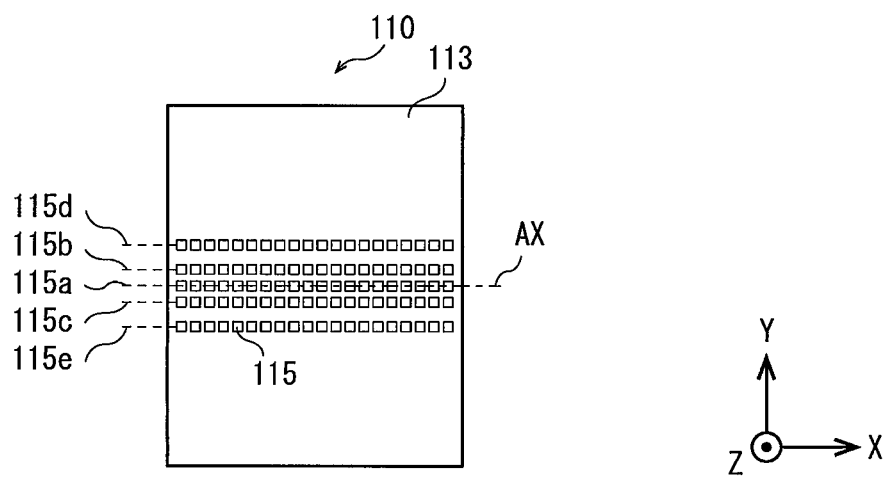

FIG. 3 is a view illustrating the configuration of the light source unit 100, FIG. 3A is a front view (a view viewed from the positive direction side of the Z axis), and FIG. 3B is a sectional view taken along the line A-A of FIG. 3A. As illustrated in FIG. 3, the light source unit 100 has a box-shaped case 102 in which a plurality of LED modules 110, a heat sink 120, a lens 150, and the like are housed. FIG. 4 is a view illustrating the configuration of the LED module 110 of the present embodiment, FIG. 4A is a front view (namely, a view of the LED module 110 of FIG. 3B viewed from the positive direction side of the Z axis), and FIG. 4B is an enlarged view of the LED module 110. Incidentally, in the present specification, a straight line bisecting the LED module 110 in the Y-axis direction is defined as a straight line AX as illustrated in FIG. 4B and a straight line which is perpendicular to the straight line AX and parallel to the Z-axis direction is defined as a straight line BX (perpendicular line passing through the center of the LED module 110) as illustrated in FIG. 3B for convenience of explanation.

As illustrated in FIG. 3, a rectangular opening 102b is formed on a front panel 102a (the end face in the Z-axis direction) of the case 102 and linear ultraviolet light is emitted through the lens 150 disposed in the opening 102b.

The heat sink 120 is a so-called air-cooled heat sink which is disposed so as to be in close contact with the back surface of a substrate 113 of the LED module 110 and dissipates heat generated in each LED module 110. The heat sink 120 is formed of a material having a favorable thermal conductivity such as aluminum or copper and equipped with a thin plate-shaped base plate 122 extending in the X-axis direction and a plurality of heat dissipation fins 125 formed on the surface opposite to the surface on which the substrate 113 abuts. Each heat dissipation fins 125 has a thin plate shape parallel to the Y-Z plane and is provided at a predetermined interval in the X-axis direction. Incidentally, the plurality of heat dissipation fins 125 are uniformly cooled by the air current to be generated by a cooling fan (not illustrated) in the present embodiment.

As illustrated in FIG. 4B, the LED module 110 is equipped with the rectangular substrate 113 parallel to the X-axis direction and the Y-axis direction and a plurality of LED elements 115 disposed on the substrate 113, and in the present embodiment, four LED modules 110 are disposed on the surface of the heat sink 120 side by side in the X-axis direction as illustrated in FIG. 4A.

The substrate 113 of each LED module 110 is a rectangular wiring substrate formed of a material having a high thermal conductivity (for example, aluminum nitride), and the LED elements 115 of five rows (Y-axis direction)×20 pieces (X-axis direction) are mounted on the surface thereof by COB (Chip On Board) as illustrated in FIG. 4B. Incidentally, in the present specification, the LED elements 115 to be disposed in each row are referred to as LED elements 115a, 115b, 115c, 115d, and 115e as illustrated in FIG. 4B for convenience of explanation. In other words, one row of LED elements 115 to be disposed at substantially the center in the Y-axis direction of the substrate 113 (namely, to be disposed along the straight line AX) is referred to as the LED elements 115a, and two rows separated from the LED elements 115a in the positive direction of the Y axis are referred to as the LED elements 115b and 115d and two rows separated from the LED elements 115a in the negative direction of the Y axis are referred to as the LED elements 115c and 115e, respectively. Incidentally, in the present embodiment, the distance between the LED element 115a and the LED element 115b and the distance between the LED element 115a and the LED element 115c are set to 2 mm, respectively, and the distance between the LED element 115b and the LED element 115d and the distance between the LED element 115c and the LED element 115e are set to 3 mm, respectively. In other words, the LED elements 115a, 115b, 115c, 115d, and 115e of the present embodiment are line-symmetrically disposed with respect to the straight line AX when viewed from the Z-axis direction.

An anode pattern (not illustrated) and a cathode pattern (not illustrated) for supplying an electric power to each LED element 115 are formed on the substrate 113, and each LED element 115 is soldered to the anode pattern and the cathode pattern, respectively, and electrically connected thereto. In addition, the substrate 113 is electrically connected to a driver circuit (not illustrated) by a wiring cable (not illustrated), and a driving current is supplied from the driver circuit to each LED element 115 via the anode pattern and the cathode pattern. Ultraviolet light (for example, a wavelength of 385 nm) having a quantity of light corresponding to the driving current is emitted from each LED element 115 and linear ultraviolet light parallel to the X-axis direction is emitted from the LED module 110 when a driving current is supplied to each LED element 115. In the present embodiment, the LED module 110 is configured such that four LED modules 110 are arranged in the X-axis direction and linear ultraviolet light is continuously emitted from each LED module 110 in the X-axis direction as illustrated in FIG. 4A. Incidentally, with regard to each LED element 115 of the present embodiment, the driving current to be supplied to each LED element 115 is adjusted so that ultraviolet light having a substantially uniform quantity of light is emitted and linear ultraviolet light to be emitted from the four LED modules 110 has substantially uniform distribution of quantity of light in the X-axis direction.

When an electric power is supplied to the LED module 110 and ultraviolet light is emitted from each LED element 115, a problem occurs that the temperature rises by self-heating of the LED element 115 and the luminous efficiency significantly decreases, but the occurrence of such a problem is suppressed in the present embodiment since the respective LED modules 110 are uniformly cooled by the heat sink 120.

The ultraviolet light to be emitted from each LED module 110 is incident on the lens 150 disposed so that the optical axis is positioned on the straight line BX (FIG. 3B). The lens 150 is a round bar-shaped glass cylindrical lens which extends in the X-axis direction and has a diameter $\phi$ of 14 mm. Ultraviolet light emitted from each of the LED elements 115a, 115b, 115c, 115d, and 115e passes through the lens 150 to be refracted in the Y-axis direction, condensed in the Y-axis direction (that is, the spread angle is narrowed), and emitted from the light source unit 100. In other words, ultraviolet light providing a high irradiation intensity is emitted from the light source unit 100.

Incidentally, a pair of third reflection portions 132 and 134 are disposed between the LED module 110 and the lens 150 so as to be separated from each other in the Y-axis direction as illustrated in FIG. 3B. The pair of third reflection portions 132 and 134 extend in the X-axis direction so as to sandwich the optical path of each ultraviolet light to be emitted from each of the LED elements 115a, 115b, 115c, 115d, and 115e from the Y-axis direction, are disposed so that reflection surfaces 132a and 134a face each other, and guide ultraviolet light to be emitted from the LED module 110 to the lens 150. Incidentally, in the present embodiment, the reflection surfaces 132a and 134a of the third reflection portions 132 and 134 are line-symmetrical to each other by taking the straight line BX as the axis of symmetry when viewed from the X-axis direction and constituted by planes which narrow toward the front side (the positive direction side of the Z axis) at a predetermined angle. Generally, ultraviolet light to be emitted from the LED element 115 has a great spread angle, but all the rays of light (ultraviolet light) to be emitted from each LED element 115 are emitted through the lens 150 since ultraviolet light having a great angular component reflects from the reflection surfaces 132a and 134a of the third reflection portions 132 and 134.

In addition, a pair of fourth reflection portions 162 and 164 are disposed between the lens 150 and the case 102 (namely, the front panel 102a) to be separated from each other in the Y-axis direction as illustrated in FIG. 3B. The pair of fourth reflection portions 162 and 164 extend in the X-axis direction so as to sandwich the optical path of ultraviolet light to be emitted from the lens 150 from the Y-axis direction, are disposed so that reflection surfaces 162a and 164a face each other, and guide ultraviolet light to be emitted from the lens 150 to the translucent pipe 200 and the mirror module 300 at the subsequent stage. Incidentally, in the present embodiment, the reflection surfaces 162a and 164a of the fourth reflection portions 162 and 164 are line-symmetrical to each other by taking the straight line BX as the axis of symmetry when viewed from the X-axis direction and constituted by planes which widen toward the front side (the positive direction side of the Z axis) at a predetermined angle. As to be described later, ultraviolet light emitted from the lens 150 enters the translucent pipe 200 and the mirror module 300 at the subsequent stage, but there is return light which reflects from the mirror module 300 and returns to the light source unit 100 side. However, according to the configuration of the present embodiment, it is possible to confine ultraviolet light in the space between the light source unit 100 and the mirror module 300 since the return light from the mirror module 300 can reflects again from the fourth reflection portions 162 and 164.

The translucent pipe 200 is a glass pipe which is capable of transmitting ultraviolet light from the light source unit 100 and has, for example, an outer diameter of 23 mm and an inner diameter of 20 mm, disposed between the lens 150 and the mirror module 300 so as to extend in the X-axis direction, and fixed by a support member (not illustrated) at both ends in the X-axis direction (FIGS. 1 and 2). Moreover, the optical fiber F moving in the X-axis direction is inserted in the translucent pipe 200. Incidentally, the optical fiber F of the present embodiment has, for example, an outer diameter $\phi$ of 0.25 mm, is disposed along the central axis of the translucent pipe 200, and moves in the X-axis direction at a speed of from 200 to 1200 m/min. In addition, in the present embodiment, the translucent pipe 200 is disposed so that the central axis thereof is positioned on the straight line BX, and the position of the optical fiber F in the Y-axis direction substantially coincides with the straight line BX.

As illustrated in FIGS. 1 and 2, the mirror module 300 is constituted by a reflection member 310, a mirror frame 320, and a cooling fan 330.

Figure 5:
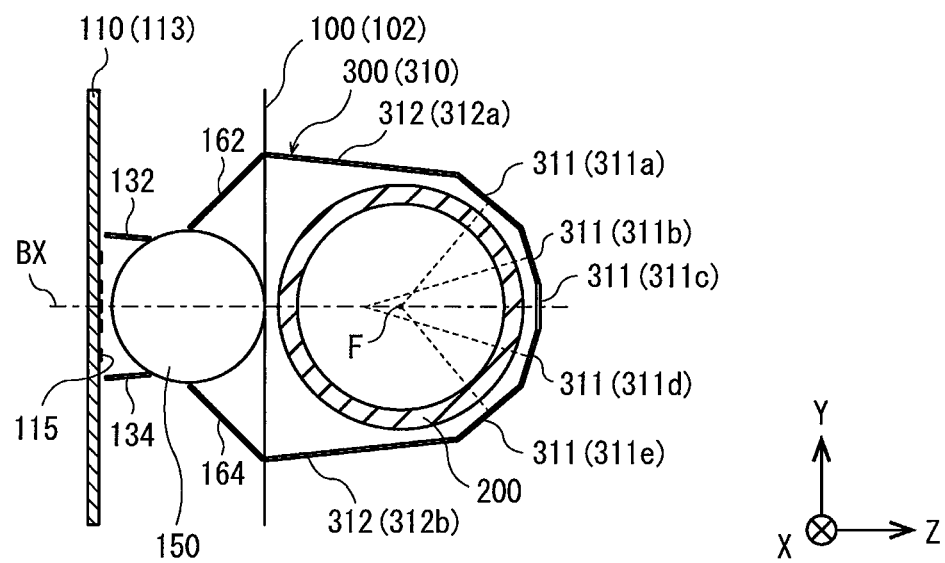
FIG. 5 is a sectional view of a Y-Z plane illustrating the positional relationship among an LED module, a translucent pipe, and a reflecting mirror of a mirror module equipped in a light irradiation device according to a first embodiment of the present invention.

FIG. 5 is a sectional view of the Y-Z plane illustrating the positional relationship among the LED module 110, the translucent pipe 200, and the reflection member 310 of the mirror module 300. Incidentally, the mirror frame 320, the heat sink 120, and the like are omitted in FIG. 5 for convenience of explanation.

As illustrated in FIG. 5, the reflection member 310 is a member which extends in the X-axis direction so as to cover the translucent pipe 200 and is disposed on the front face of the case 102. The reflection member 310 is formed by, for example, bending an elongated plate material of aluminum along the X-axis direction, and a plurality of reflection surfaces (first reflection surfaces 311a, 311b, 311c, 311d, and 311e of a first reflection portion 311 and second reflection surfaces 312a and 312b of a second reflection portion 312 to be described later) are formed on the side opposite to the translucent pipe 200.

As illustrated in FIG. 5, the reflection member 310 of the present embodiment is a member which reflects ultraviolet light to be emitted from the light source unit 100 to the optical fiber F, is bent at six places along the X-axis direction so that the cross section thereof has a substantially U-shape, and constituted by the first reflection portion 311 and the second reflection portion 312.

The second reflection portion 312 is constituted by a pair of second reflection surfaces 312a and 312b which stand upright in the Z-axis direction from the tip portions of the fourth reflection portions 162 and 164 of the light source unit 100 and guide ultraviolet light to be emitted from the light source unit 100 to the first reflection surfaces 311a, 311b, 311c, 311d, and 311e of the first reflection portion 311. Incidentally, in the present embodiment, the pair of second reflection surfaces 312a and 312b are constituted by planes which narrow toward the front side (the positive direction side of the Z axis) at a predetermined angle as illustrated in FIG. 5.

The first reflection portion 311 is constituted by five first reflection surfaces 311a, 311b, 311c, 311d, and 311e disposed on the downstream side in the Z-axis direction of the optical fiber F, and a part of ultraviolet light incident on each of the first reflection surfaces 311a, 311b, 311c, 311d, and 311e reflects to the back surface (a region to be half of the outer circumference surface positioned on the downstream side in the Z-axis direction) of the outer circumference surface of the optical fiber F. Incidentally, as illustrated in FIG. 5, each of the first reflection surfaces 311a, 311b, 311c, 311d, and 311e of the present embodiment is disposed in a circular arc shape, and is disposed so that perpendicular lines (namely, perpendicular bisectors indicated by broken lines in FIG. 5) passing through the center of each of the first reflection surfaces 311a, 311b, 311c, 311d, and 311e intersect the straight line BX.

Figure 6A:
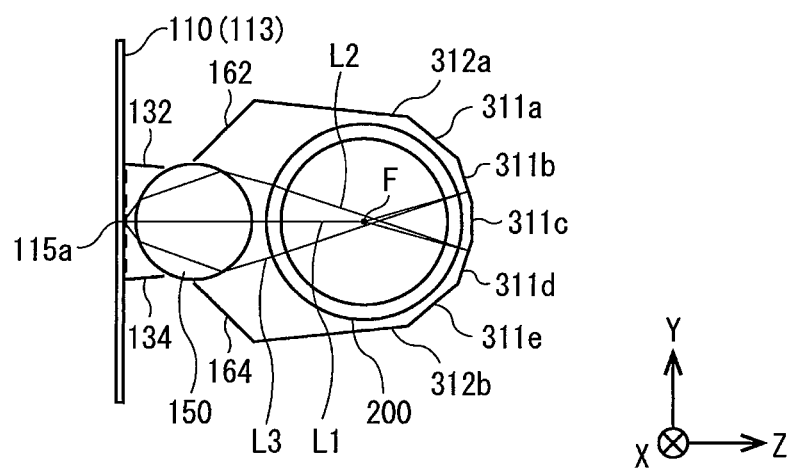
FIGS. 6A to 6C are views of rays of ultraviolet light to be emitted from a light source unit of a light irradiation device according to a first embodiment of the present invention.
Figure 6B:
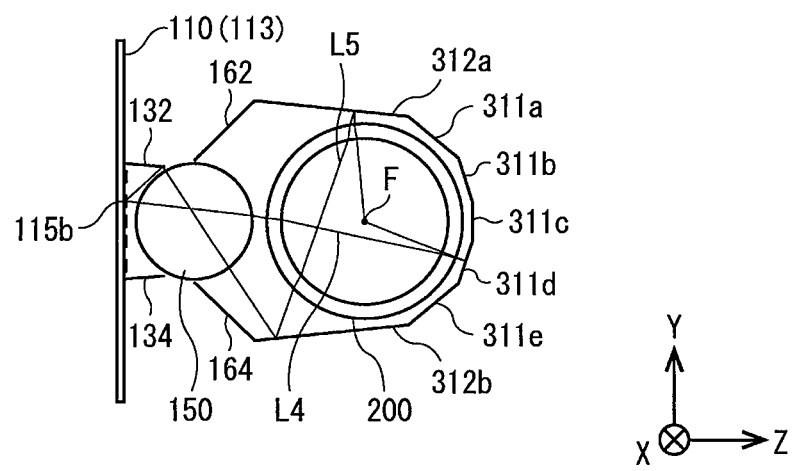
Figure 6C:
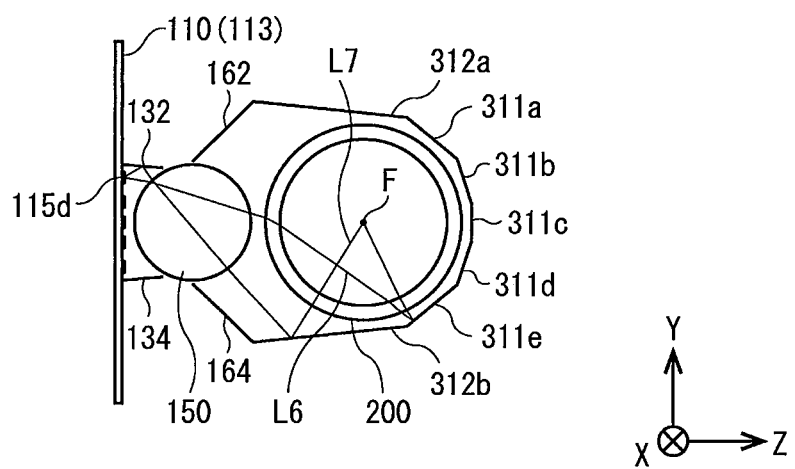

FIG. 6 is a view of a ray of ultraviolet light to be emitted from the light source unit 100 of the present embodiment, FIG. 6A illustrates an example of a ray of light to be emitted from the LED element 115a and incident on the outer circumference surface of the optical fiber F, FIG. 6B illustrates an example of a ray of light to be emitted from the LED element 115b and incident on the outer circumference surface of the optical fiber F, and FIG. 6C illustrates an example of a ray of light to be emitted from the LED element 115d and incident on the outer circumference surface of the optical fiber F. Incidentally, the LED elements 115a, 115b, 115c, 115d, and 115e of the present embodiment are disposed to be line-symmetrical with respect to the straight line AX when viewed from the Z-axis direction as described above, and the rays of ultraviolet light to be emitted from the LED element 115b and the rays of ultraviolet light to be emitted from the LED element 115c are thus line-symmetrical with respect to the straight line BX. Hence, the description on the rays of light to be emitted from the LED element 115c will be omitted. In addition, the rays of ultraviolet light to be emitted from the LED element 115d and the rays of the ultraviolet light to be emitted from the LED element 115e are line-symmetrical with respect to the straight line BX and the description on the rays of light to be emitted from the LED element 115e will be thus omitted in the same manner.

L1 in FIG. 6A is the principal ray of light (namely, the ray of light having the highest illuminance) which has an angle component of 0° and is emitted from the LED element 115a of the light source unit 100, L2 is a ray of light which has an angle component of +60° and is emitted from the LED element 115a of the light source unit 100, and L3 is a ray of light which has an angle component of −60° and is emitted from the LED element 115a of the light source unit 100. The ray of light L1 to be emitted from the LED element 115a of the light source unit 100 passes through the lens 150 without being refracted and is emitted from the lens 150. Thereafter, the ray of light L1 emitted from the lens 150 directly enters the interior of the translucent pipe 200, and the front surface (a region to be half of the outer circumference surface positioned on the upstream side (negative direction side) in the Z-axis direction) of the outer circumference surface of the optical fiber F is irradiated with the ray of light L1. In addition, the ray of light L2 to be emitted from the LED element 115a of the light source unit 100 is refracted by the lens 150 and emitted from the lens 150. Thereafter, the ray of light L2 emitted from the lens 150 passes through the translucent pipe 200, reflects from the first reflection surface 311d, and then enters the interior of the translucent pipe 200 again, and the back surface (a region to be half of the outer circumference surface positioned on the downstream side (positive direction side) in the Z-axis direction) of the outer circumference surface of the optical fiber F is irradiated with the ray of light L2. In addition, the ray of light L3 to be emitted from the LED element 115a of the light source unit 100 is refracted by the lens 150 and emitted from the lens 150. Thereafter, the ray of light L3 emitted from the lens 150 passes through the translucent pipe 200, reflects from the first reflection surface 311b, and then enters the interior of the translucent pipe 200 again, and the back surface (a region to be half of the outer circumference surface positioned on the downstream side (positive direction side) in the Z-axis direction) of the outer circumference surface of the optical fiber F is irradiated with the ray of light L3. As described above, the rays of light to be emitted from the LED element 115a of the present embodiment pass through the lens 150 and are then incident on the entire outer circumference surface of the optical fiber F directly or by reflecting from the first reflection portion 311. In other words, ultraviolet light providing a high irradiation intensity is incident on the entire outer circumference surface of the optical fiber F.

L4 in FIG. 6B is a principal ray of light which has an angle component of 0° and is emitted from the LED element 115b of the light source unit 100, and L5 is a ray of light which has an angle component of +45° and is emitted from the LED element 115b of the light source unit 100. The ray of light L4 to be emitted from the LED element 115b of the light source unit 100 is refracted by the lens 150 and emitted from the lens 150. Thereafter, the ray of light L4 emitted from the lens 150 passes through the translucent pipe 200, reflects from the first reflection surface 311d, and then enters the interior of the translucent pipe 200 again, and the back surface (a region to be half of the outer circumference surface positioned on the downstream side (positive direction side) in the Z-axis direction) of the outer circumference surface of the optical fiber F is irradiated with the ray of light L4. In addition, the ray of light L5 to be emitted from the LED element 115b of the light source unit 100 reflects from the third reflection portion 132, then passes through the lens 150, and is emitted from the lens 150. Thereafter, the ray of light L5 emitted from the lens 150 passes through the translucent pipe 200, reflects from the second reflection surface 312a, and then enters the interior of the translucent pipe 200 again, and the side surface (a region to be half of the outer circumference surface positioned on the positive direction side in the Y-axis direction) of the outer circumference surface of the optical fiber F is irradiated with the ray of light L5. As described above, the rays of light to be emitted from the LED element 115b of the present embodiment are guided by the third reflection portions 132 and 134 and pass through the lens 150. Thereafter, the rays of light having passed through the lens 150 are further guided by the fourth reflection portions 162 and 164, reflect from the first reflection portion 311 and the second reflection portion 312, and are incident on the entire outer circumference surface of the optical fiber F. In other words, ultraviolet light providing a high irradiation intensity is incident on the entire outer circumference surface of the optical fiber F.

L6 in FIG. 6C is a principal ray of light which has an angle component of 0° and is emitted from the LED element 115d of the light source unit 100, and L7 is a ray of light which has an angle component of +45° and is emitted from the LED element 115d of the light source unit 100. The ray of light L6 to be emitted from the LED element 115d of the light source unit 100 is refracted by the lens 150 and emitted from the lens 150. Thereafter, the ray of light L6 emitted from the lens 150 passes through the translucent pipe 200, reflects from the first reflection surface 311e, and then enters the interior of the translucent pipe 200 again, and the back surface (a region to be half of the outer circumference surface positioned on the downstream side (positive direction side) in the Z-axis direction) of the outer circumference surface of the optical fiber F is irradiated with the ray of light L6. In addition, the ray of light L7 to be emitted from the LED element 115d of the light source unit 100 reflects from the third reflection portion 132, is then refracted by the lens 150, and emitted from the lens 150. Thereafter, the ray of light L7 emitted from the lens 150 passes through the translucent pipe 200, reflects from the second reflection surface 312b, and then enters the interior of the translucent pipe 200 again, and the front surface (a region to be half of the outer circumference surface positioned on the upstream side (negative direction side) in the Z-axis direction) of the outer circumference surface of the optical fiber F is irradiated with the ray of light L7. As described above, the rays of light to be emitted from the LED element 115d of the present embodiment are guided by the third reflection portions 132 and 134 and pass through the lens 150. Thereafter, the rays of light having passed through the lens 150 are further guided by the fourth reflection portions 162 and 164, reflect from the first reflection portion 311 and the second reflection portion 312, and are incident on the entire outer circumference surface of the optical fiber F. In other words, ultraviolet light providing a high irradiation intensity is incident on the entire outer circumference surface of the optical fiber F.

As described above, the principal ray of light to be emitted from the LED element 115a of the present embodiment passes through the lens 150 without being refracted and the front surface (a region to be half of the outer circumference surface positioned on the upstream side (negative direction side) in the Z-axis direction) of the outer circumference surface of the optical fiber F is irradiated with the principal ray of light. In addition, the principal rays of light to be emitted from the LED elements 115b, 115c, 115d, and 115e of the present embodiment are shifted from the optical axis (namely, the straight line BX) of the lens 150, thus refracted by the lens 150, and reflect from the first reflection portion 311, and the back surface (a region to be half of the outer circumference surface positioned on the downstream side (positive direction side) in the Z-axis direction) of the outer circumference surface of the optical fiber F is irradiated with the principal rays of light. Incidentally, in the present embodiment, the light irradiation device is configured so that the interval of the LED elements 115a, 115b, 115c, 115d, and 115e in the Y-axis direction widens as the distance from the center (namely, the LED element 115a) of the LED module 110 increases, and the principal rays of light to be emitted from the LED elements 115b, 115c, 115d, and 115e are incident on the entire outer circumference surface of the optical fiber F since these reflect from the different first reflection surfaces, respectively. In addition, the rays of light other than the principal rays of light to be emitted from the LED elements 115a, 115b, 115c, 115d, and 115e of the present embodiment are also guided by the third reflection portions 132 and 134, refracted by the lens 150, further guided by the fourth reflection portions 162 and 164, reflect from the first reflection portion 311 and the second reflection portion 312, and are incident on the entire outer circumference surface of the optical fiber F. In other words, ultraviolet light to be emitted from each of the LED elements 115a, 115b, 115c, 115d, and 115e is confined in the space between the light source unit 100 and the mirror module 300 and incident on the entire outer circumference surface of the optical fiber F from the various directions. Hence, according to such configuration of the present embodiment, it is possible to irradiate the entire outer circumference surface of the optical fiber F with ultraviolet light providing a high irradiation intensity. In addition, ultraviolet light directed in various directions exists in the space between the light source unit 100 and the mirror module 300 and the entire outer circumference surface of the optical fiber F is thus irradiated with ultraviolet light even if the optical fiber F runs to be slightly shifted from the central axis of the translucent pipe 200.

Returning to FIG. 1 and FIG. 2, the mirror frame 320 of the mirror module 300 is a metallic plate-shaped member which dissipates the heat of the reflection member 310 as well as supports the reflection member 310. A concave portion 322 (housing portion) which houses the reflection member 310 and the translucent pipe 200 is formed on one end face (the face on the side opposite to the light source unit 100) of the mirror frame 320, and the reflection member 310 and the translucent pipe 200 are housed and fixed in the concave portion 322 when the mirror module 300 is attached to the front panel 102a of the case 102. Moreover, when the reflection member 310 is housed and fixed in the concave portion 322, the mirror frame 320 is brought into close contact with and thermally bonded to the first reflection portion 311 and the second reflection portion 312 of the reflection member 310. A plurality of heat dissipation fins 324 which efficiently dissipate the heat of the mirror frame 320 are formed on the other end face of the mirror frame 320. Hence, the heat conducted from the reflection member 310 to the mirror frame 320 is efficiently dissipated into the air via the heat dissipation fins 324.

The cooling fan 330 is a device which cools the heat dissipation fins 324 of the mirror frame 320. Since the external air is blown to the heat dissipation fins 324 by the cooling fan 330, the heat dissipation fins 324 are further more efficiently cooled as compared to natural air cooling.

Figure 7A:
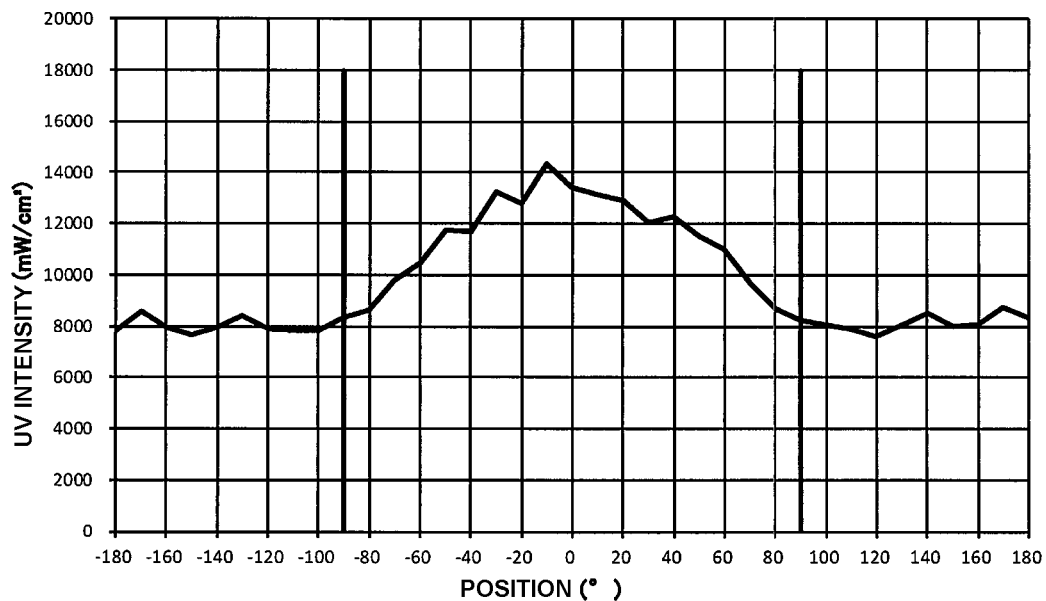
FIGS. 7A and 7B are views illustrating the simulation results on the distribution of intensity of ultraviolet light on an outer circumference surface of an optical fiber F to be irradiated by a light irradiation device according to a first embodiment of the present invention.
Figure 7B:
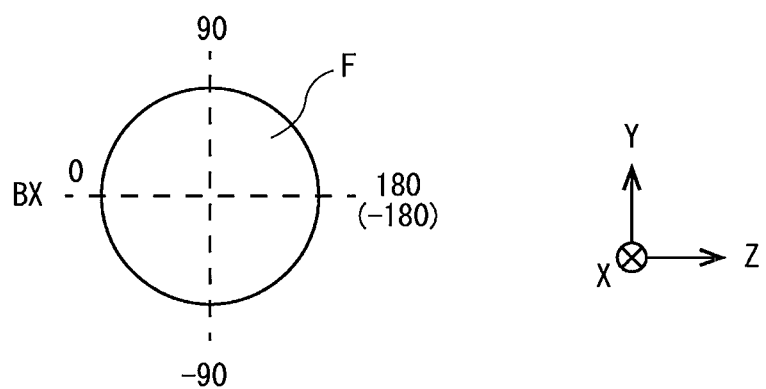

Next, the intensity of ultraviolet light on the outer circumference surface of the optical fiber F to be irradiated by the light irradiation device 1 of the present embodiment will be described. FIG. 7 is a view illustrating the simulation results on the distribution of intensity of ultraviolet light on the outer circumference surface of the optical fiber F to be irradiated by the light irradiation device 1 of the present embodiment, FIG. 7A is a graph illustrating the distribution of intensity of ultraviolet light at the central portion in the X-axis direction of the translucent pipe 200, and FIG. 7B is a view illustrating the horizontal axis of FIG. 7A. As illustrated in FIG. 7B, the horizontal axis of FIG. 7A represents the position of the outer circumference surface when the position at which the outer circumference surface of the optical fiber F intersects the straight line BX (FIG. 5) is 0°, the clockwise angle is indicated by from 0° to 180° (namely, +), and the counterclockwise angle is indicated by from 0° to −180° (namely, −). Incidentally, the vertical axis in FIG. 7A represents the intensity of ultraviolet light (mW/cm$^2$).

As illustrated in FIG. 7, it can be seen that a predetermined intensity (for example, 6000 (mW/cm$^2$)) to be required to cure the coating agent coated on the outer circumference surface of the optical fiber F is obtained as a whole although the intensity of ultraviolet light at which the front surface (0° to −90° and 0° to 90°) of the outer circumference surface of the optical fiber F is irradiated is slightly higher than the intensity of ultraviolet light at which the back surface (−180° to −90° and 180° to 90°) of the outer circumference surface of the optical fiber F is irradiated. Incidentally, in the present embodiment, the maximum value of the intensity of ultraviolet light on the outer circumference surface of the optical fiber F is 14340 (mW/cm$^2$), the minimum value thereof is 7617 (mW/cm$^2$), and the ratio of the minimum value to the maximum value is 53.1%.

As described above, according to the configuration of the present embodiment, it is possible to irradiate the entire outer circumference surface of the optical fiber F with ultraviolet light having a high irradiation intensity. As a result, the coating agent coated on the outer circumference surface of the optical fiber F is uniformly cured. In addition, according to the configuration of the present embodiment, the distance (about 10 mm) between the light source unit 100 and the optical fiber F can be remarkably shortly set as compared to the conventional configuration using an elliptical mirror, and the light irradiation device 1 which is smaller in size as compared to the prior art is realized.

The present embodiment has been described above, but the present invention is not limited to the configuration described above, and various modifications are possible within the scope of the technical idea of the present invention.

For example, the light irradiation device 1 of the present embodiment has been described as a light irradiation device which cures the coating agent coated on a drawn optical fiber F, but the application of the light irradiation device 1 is not limited thereto. For example, the irradiation target may have a linear, spherical or granular shape, and it is possible to cure the coating agent coated on the outer circumference surface of the irradiation target in this case as well. In addition, for example, the irradiation target may be liquid, and the irradiation target can be sterilized by being irradiated with ultraviolet light in this case.

In addition, in the present embodiment, the optical fiber F moving (running) in one direction is used as the irradiation target, but the irradiation target is not necessarily required to move, and the light irradiation device 1 can also be configured to irradiate a stopped irradiation target with ultraviolet light.

In addition, in the present embodiment, the light irradiation device 1 is configured to use the LED elements 115 arranged in the form of five rows (Y-axis direction)×20 pieces (X-axis direction), but the present invention is not limited to such configuration, and the LED elements 115 may be disposed in the form of M rows (M is an integer 2 or greater). In addition, M first reflection surfaces on which the principal rays of light from the LED elements 115 in each row are incident may be formed in this case. In addition, the light irradiation device 1 can also be configured so that a plurality of principal rays of light are incident on one first reflection surface, and there may be two or more first reflection surfaces.

In addition, the lens 150 of the present embodiment is a round bar-shaped cylindrical lens, but it can also be a cylindrical lens of which at least one surface is a convex surface. In addition, the lens 150 is not necessarily required to be spherical, and it may be aspherical.

In addition, in the present embodiment, the reflection surfaces 132a and 134a of the third reflection portions 132 and 134 are constituted by planes which narrow toward the front side (the positive direction side of the Z axis) at a predetermined angle when viewed from the X-axis direction, but the reflection surfaces 132a and 134a may be parallel to the Z-axis direction when viewed from the X-axis direction as long as the light spreading outward (the positive direction side and the negative direction side of the Y axis) can be turned back inward (the straight line BX side).

Second Embodiment

Figure 8:
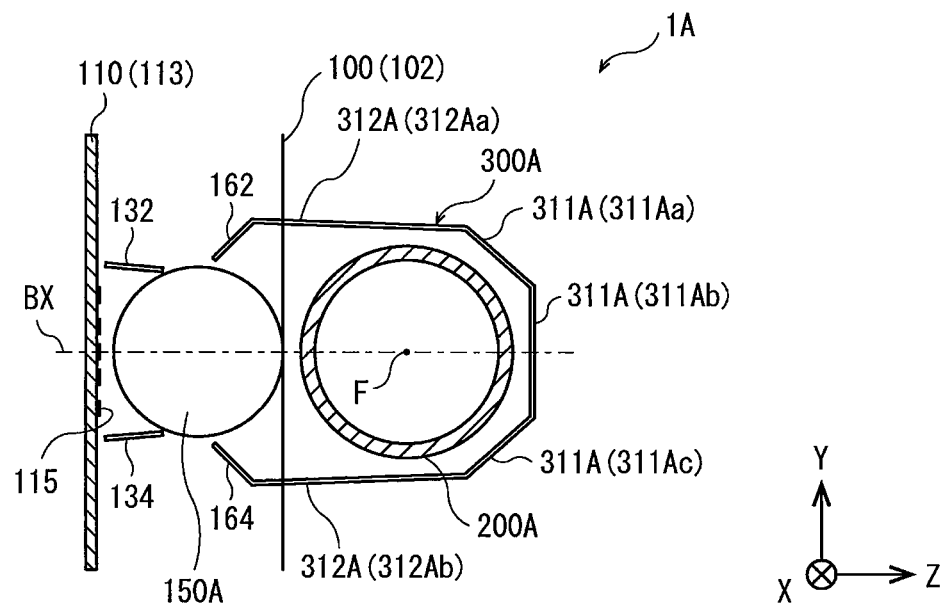
FIG. 8 is a sectional view illustrating the configuration of a light irradiation device according to a second embodiment of the present invention.

FIG. 8 is a sectional view illustrating the configuration of a light irradiation device 1A according to a second embodiment of the present invention. Incidentally, the mirror frame 320, the heat sink 120, and the like are omitted in FIG. 8 for convenience of explanation. The light irradiation device 1A of the present embodiment differs from the light irradiation device 1 of the first embodiment in that a lens 150A and a translucent pipe 200A are constituted to be thin and three first reflection surfaces 311Aa, 311Ab, and 311Ac are formed on a first reflection portion 311A of a mirror module 300A. Incidentally, the light irradiation device 1A is also equipped with a second reflection portion 312A which is constituted by a pair of second reflection surfaces 312Aa and 312Ab which stand upright in the Z-axis direction from the tip portions of the fourth reflection portions 162 and 164 of the light source unit 100 and guide ultraviolet light to be emitted from the light source unit 100 to the first reflection surfaces 311Aa, 311Ab, and 311Ac of the first reflection portion 311A in the same manner as the light irradiation device 1 of the first embodiment.

Figure 9A:
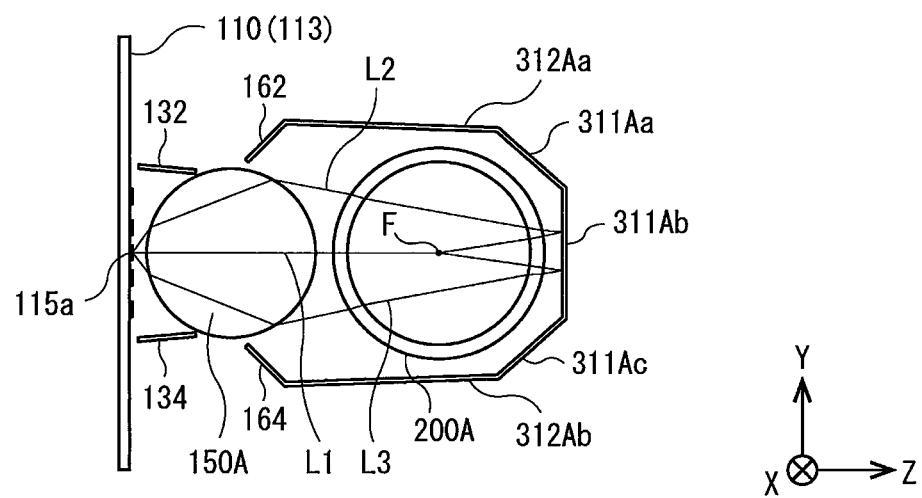
FIGS. 9A to 9C are views of rays of ultraviolet light to be emitted from a light source unit of a light irradiation device according to a second embodiment of the present invention.
Figure 9B:
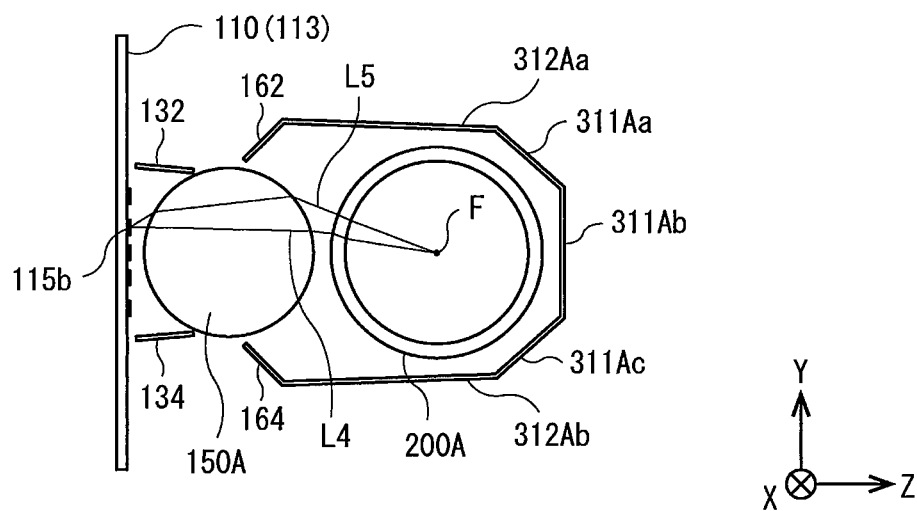
Figure 9C:
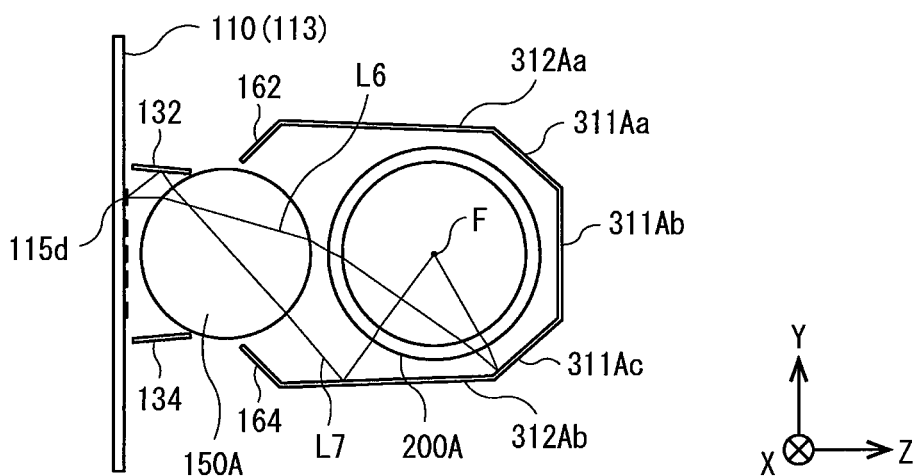

FIG. 9 is a view of rays of ultraviolet light of the present embodiment, and FIG. 9A illustrates an example of a ray of light to be emitted from the LED element 115a and incident on the outer circumference surface of the optical fiber F, FIG. 9B illustrates an example of a ray of light to be emitted from the LED element 115b and incident on the outer circumference surface of the optical fiber F, and FIG. 9C illustrates an example of a ray of light to be emitted from the LED element 115d and incident on the outer circumference surface of the optical fiber F. Incidentally, the description on the rays of light to be emitted from the LED element 115c and the rays of light to be emitted from the LED element 115e will be omitted in the same manner as in the first embodiment.

L1 in FIG. 9A is the principal ray of light (namely, the ray of light having the highest illuminance) which has an angle component of 0° and is emitted from the LED element 115a of the light source unit 100, L2 is a ray of light which has an angle component of +60° and is emitted from the LED element 115a of the light source unit 100, and L3 is a ray of light which has an angle component of −60° and is emitted from the LED element 115a of the light source unit 100. The ray of light L1 to be emitted from the LED element 115a passes through the lens 150A without being refracted and is emitted from the lens 150A. Thereafter, the ray of light L1 emitted from the lens 150A directly enters the interior of the translucent pipe 200A, and the front surface (a region to be half of the outer circumference surface positioned on the upstream side (negative direction side) in the Z-axis direction) of the outer circumference surface of the optical fiber F is irradiated with the ray of light L1. In addition, the ray of light L2 to be emitted from the LED element 115a is refracted by the lens 150A and emitted from the lens 150A. Thereafter, the ray of light L2 emitted from the lens 150A passes through the translucent pipe 200A, reflects from the first reflection surface 311Ab, and then enters the interior of the translucent pipe 200A again, and the back surface (a region to be half of the outer circumference surface positioned on the downstream side (positive direction side) in the Z-axis direction) of the outer circumference surface of the optical fiber F is irradiated with the ray of light L2. In addition, the ray of light L3 to be emitted from the LED element 115a is refracted by the lens 150A and emitted from the lens 150A. Thereafter, the ray of light L3 emitted from the lens 150A passes through the translucent pipe 200A, reflects from the first reflection surface 311Ab, and then enters the interior of the translucent pipe 200A again, and the back surface (a region to be half of the outer circumference surface positioned on the downstream side (positive direction side) in the Z-axis direction) of the outer circumference surface of the optical fiber F is irradiated with the ray of light L3. As described above, the rays of light which have an angle component of 0° and ±60° and are emitted from the LED element 115a of the present embodiment pass through the lens 150A, and are then incident on the entire outer circumference surface of the optical fiber F directly or by reflecting from the first reflection surface 311Ab.

L4 in FIG. 9B is a principal ray of light which has an angle component of 0° and is emitted from the LED element 115b, and L5 is a ray of light which has an angle component of +45° and is emitted from the LED element 115b. The ray of light L4 to be emitted from the LED element 115b is refracted by the lens 150A and emitted from the lens 150A. Thereafter, the ray of light L4 emitted from the lens 150A enters the interior of the translucent pipe 200A, and the front surface (a region to be half of the outer circumference surface positioned on the upstream side (negative direction side) in the Z-axis direction) of the outer circumference surface of the optical fiber F is irradiated with the ray of light L4. In addition, the ray of light L5 to be emitted from the LED element 115b is refracted by the lens 150A and is emitted from the lens 150A. Thereafter, the ray of light L5 emitted from the lens 150A enters the interior of the translucent pipe 200A, and the front surface (a region to be half of the outer circumference surface positioned on the upstream side (negative direction side) in the Z-axis direction) of the outer circumference surface of the optical fiber F is irradiated with the ray of light L5. As described above, the rays of light which have an angle component of 0° and +45° and are emitted from the LED element 115b of the present embodiment pass through the lens 150A and are directly incident on the outer circumference surface of the optical fiber F.

L6 in FIG. 9C is a principal ray of light which has an angle component of 0° and is emitted from the LED element 115d, and L7 is a ray of light which has an angle component of +45° and is emitted from the LED element 115d. The ray of light L6 to be emitted from the LED element 115d is refracted by the lens 150A and emitted from the lens 150A. Thereafter, the ray of light L6 emitted from the lens 150A passes through the translucent pipe 200A, reflects from the first reflection surface 311Ac, and then enters the interior of the translucent pipe 200A again, and the back surface (a region to be half of the outer circumference surface positioned on the downstream side (positive direction side) in the Z-axis direction) of the outer circumference surface of the optical fiber F is irradiated with the ray of light L6. In addition, the ray of light L7 to be emitted from the LED element 115d reflects from the third reflection portion 132, is then refracted by the lens 150A, and emitted from the lens 150A. Thereafter, the ray of light L7 emitted from the lens 150A reflects from the second reflection surface 312Ab and then enters the interior of the translucent pipe 200A, and the front surface (a region to be half of the outer circumference surface positioned on the upstream side (negative direction side) in the Z-axis direction) of the outer circumference surface of the optical fiber F is irradiated with the ray of light L7. As described above, the rays of light which have an angle component of 0° and +45° and are emitted from the LED element 115d of the present embodiment are guided by the third reflection portions 132 and 134 and pass through the lens 150A. Thereafter, the rays of light having passed through the lens 150A further reflect from the first reflection portion 311 and the second reflection portion 312, and are incident on the outer circumference surface of the optical fiber F.

As described above, in the configuration of the present embodiment as well, ultraviolet light to be emitted from each of the LED elements 115a, 115b, 115c, 115d, and 115e is confined in the space between the light source unit 100 and the mirror module 300 and incident on the outer circumference surface of the optical fiber F from the various directions in the same manner as in the first embodiment. Hence, according to such configuration of the present embodiment, it is possible to irradiate the entire outer circumference surface of the optical fiber F with ultraviolet light providing a high irradiation intensity. In addition, ultraviolet light directed in various directions exists in the space between the light source unit 100 and the mirror module 300A and the entire outer circumference surface of the optical fiber F is thus irradiated with ultraviolet light even if the optical fiber F runs to be slightly shifted from the central axis of the translucent pipe 200A.

Figure 10:
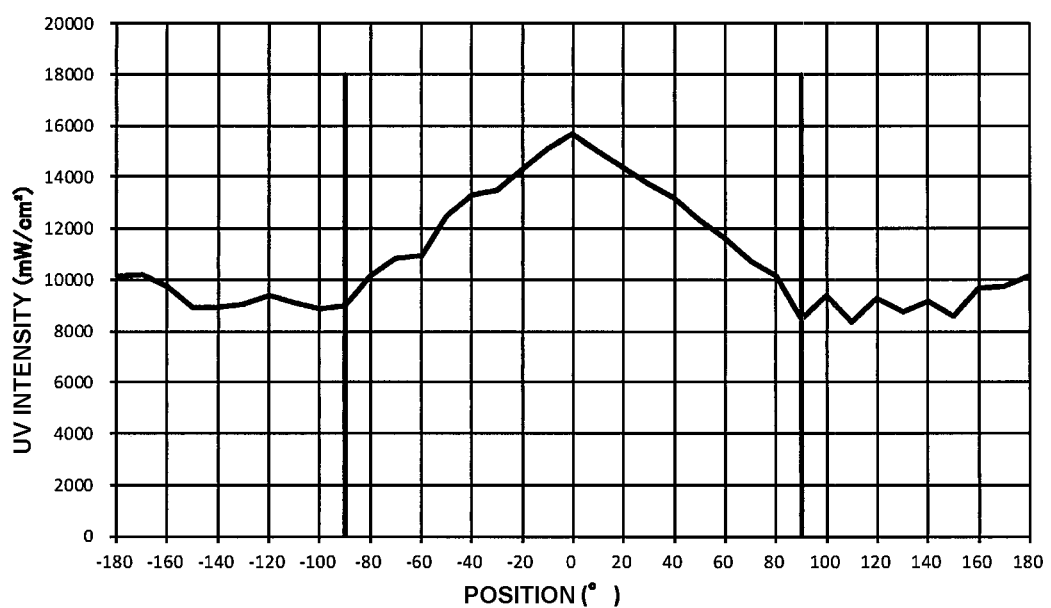
FIG. 10 is a view illustrating the simulation results on the distribution of intensity of ultraviolet light on an outer circumference surface of an optical fiber F to be irradiated by a light irradiation device according to a second embodiment of the present invention.

FIG. 10 is a view illustrating the simulation results on the distribution of intensity of ultraviolet light on the outer circumference surface of the optical fiber F to be irradiated by the light irradiation device 1A of the present embodiment. As illustrated in FIG. 10, it can be seen that a predetermined intensity (for example, 8000 (mW/cm$^2$)) to be required to cure the coating agent coated on the outer circumference surface of the optical fiber F is obtained as a whole although the intensity of ultraviolet light at which the front surface (0° to −90° and 0° to 90°) of the outer circumference surface of the optical fiber F is irradiated is slightly higher than the intensity of ultraviolet light at which the back surface (−180° to −90° and 180° to 90°) of the outer circumference surface of the optical fiber F is irradiated. Incidentally, in the present embodiment, the maximum value of the intensity of ultraviolet light on the outer circumference surface of the optical fiber F is 15647 (mW/cm$^2$), the minimum value thereof is 8352 (mW/cm$^2$), and the ratio of the minimum value to the maximum value is 53.4%.

As described above, according to the respective configurations of the first embodiment and the second embodiment of the present invention, it is possible to irradiate the entire outer circumference surface of the optical fiber F with ultraviolet light and to obtain a predetermined intensity to be required to cure the coating agent coated on the outer circumference surface of the optical fiber F. Moreover, it can be seen that the following Mathematical Formula (1) is satisfied when the maximum intensity of ultraviolet light on the outer circumference surface of the optical fiber F is denoted by MAX and the minimum intensity thereof is denoted by MIN.

$$\text{MIN/MAX} \geq 50\% \tag{1}$$

Incidentally, it should be considered that the embodiments disclosed this time are an example in all respects and are not restrictive. The scope of the present invention is not limited to the above description but is indicated by the claims and is intended to include meanings equivalent to the claims and all modifications within the scope.

DETAILED DESCRIPTION OF MAIN ELEMENTS 1 and 1A Light irradiation device
100 Light source unit
102 Case
102a Front panel
102b Opening
110 LED module
113 Substrate 115, 115a, 115b, 115c, 115d, and 115e LED element
120 Heat sink
122 Base plate
125 Heat dissipation fin
132 and 134 Third reflection portion
132a and 134a Reflection surface
150 and 150A lens
162 and 164 Fourth reflection portion
162a and 164a Reflection surface
200 and 200A Translucent pipe
300 and 300A Mirror module
310 Reflection member
311 and 311A First reflection portion
311a, 311b, 311c, 311d, 311e, 311Aa, 311Ab, and 311Ac First reflection surface
312 and 312A Second reflection portion
312a, 312b, 312Aa, and 312Ab Second reflection surface
320 Mirror frame
322 Concave portion
324 Heat dissipation fin
330 Cooling fan

The invention claimed is:

1. A light irradiation device for irradiating an irradiation target capable of relatively moving along a first direction with light, the light irradiation device comprising:
a substrate to be defined by the first direction and a second direction orthogonal to the first direction;
a light source having a plurality of solid-state elements which are disposed on the substrate in a plurality of rows along the first direction and irradiate the irradiation target with the light from a third direction orthogonal to the first direction and the second direction;
an optical element which is disposed in an optical path of the plurality of solid-state elements and refracts light from each of the solid-state elements at a predetermined angle and emits the light as well as narrows a spread angle of light to be emitted from each of the solid-state elements with respect to the third direction;
a first reflection portion which has at least two first reflection surfaces disposed on a downstream side in the third direction of the irradiation target when viewed from the first direction and reflects a part of light incident on the first reflection surface from the optical element to the irradiation target; and
a second reflection portion which has a pair of second reflection surfaces disposed between the optical element and the first reflection portion and guides the light from the optical element to the first reflection surface.

2. The light irradiation device according to claim 1, wherein a principal ray of the light to be emitted from the plurality of solid-state elements is incident on the first reflection surface or incident on the irradiation target without being incident on the first reflection surface when viewed from the first direction.

3. The light irradiation device according to claim 1, wherein a perpendicular line passing through a center of the light source substantially coincides with an optical axis of the optical element when viewed from the first direction.

4. The light irradiation device according to claim 3, wherein an interval between the plurality of solid-state elements in the second direction widens as a distance from a center of the light source increases.

5. The light irradiation device according to claim 1, wherein the optical element is a cylindrical lens extending in the first direction.

6. The light irradiation device according to claim 1, comprising a pair of third reflection portions which are disposed between the light source and the optical element so as to sandwich an optical path of the plurality of solid-state elements from the second direction and guide the light from the light source to the optical element.

7. The light irradiation device according to claim 6, wherein the pair of third reflection portions are inclined with respect to the third direction when viewed from the first direction and an interval between the pair of third reflection portions narrows as a distance from the light source increases.

8. The light irradiation device according to claim 1, comprising a pair of fourth reflection portions to be disposed between the optical element and the second reflection portion so as to sandwich an optical path of the plurality of solid-state elements from the second direction.

9. The light irradiation device according to claim 8, wherein the pair of fourth reflection portions are inclined with respect to the third direction when viewed from the first direction and an interval between the pair of fourth reflection portions widens as a distance from the optical element increases.

10. The light irradiation device according to claim 1, wherein the first reflection surface is disposed line-symmetrically with respect to a perpendicular line passing through a center of the light source when viewed from the first direction.

11. The light irradiation device according to claim 10, wherein the first reflection surface is a flat surface and is disposed so that a perpendicular bisector of the first reflection surface intersects a perpendicular line passing through a center of the light source when viewed from the first direction.

12. The light irradiation device according to claim 1, wherein the pair of second reflection surfaces are inclined with respect to the third direction when viewed from the first direction and an interval between the pair of second reflection surfaces narrows as a distance from the light source increases.

13. The light irradiation device according to claim 1, wherein the following Mathematical Formula (1) is satisfied when a maximum intensity of the light on an outer circumference surface of the irradiation target is denoted by MAX and a minimum intensity of the light on the outer circumference surface of the irradiation target is denoted by MIN:

$$\text{MIN/MAX} \geq 50\% \qquad (1).$$

14. The light irradiation device according to claim 1, comprising a heat dissipation member which is thermally bonded to the first reflection portion and the second reflection portion and dissipates heat from the first reflection portion and the second reflection portion.

15. The light irradiation device according to claim 14, wherein the heat dissipation member has a plate shape and a housing portion for housing the first reflection portion and the second reflection portion is formed on one surface of the heat dissipation member.

16. The light irradiation device according to claim 15, wherein the heat dissipation member has a plurality of heat dissipation fins on the other surface opposite to the one surface.

17. The light irradiation device according to claim 16, comprising a cooling fan for blowing air to the heat dissipation fins.

18. The light irradiation device according to claim 1, further comprising a translucent pipe which extends in the first direction so as to cover the irradiation target and transmits the light from the light source.

19. The light irradiation device according to claim 1, wherein the light is light in an ultraviolet wavelength region.

20. The light irradiation device according to claim 19, wherein the irradiation target has a linear, spherical, or granular shape and light in the ultraviolet wavelength region cures a coating agent coated on an outer circumference surface of the irradiation target.

21. The light irradiation device according to claim 19, wherein the irradiation target is liquid and light in the ultraviolet wavelength region sterilizes the irradiation target.

* * * * *